(12) United States Patent
Benni (10) Patent No.: US 8,965,472 B2
(45) Date of Patent: Feb. 24, 2015

(54) METHOD AND APPARATUS FOR SPECTROPHOTOMETRIC BASED OXIMETRY

(75) Inventor: Paul Benni, Guilford, CT (US)

(73) Assignee: CAS Medical Systems, Inc.

( * ) Notice: Subject to any disclaimer, the term of this patent is extended or adjusted under 35 U.S.C. 154(b) by 1620 days.

(21) Appl. No.: 12/090,671

(22) PCT Filed: Oct. 18, 2006

(86) PCT No.: PCT/US2006/041268
§ 371 (c)(1), (2), (4) Date: Sep. 9, 2008

(87) PCT Pub. No.: WO2007/048039
PCT Pub. Date: Apr. 26, 2007

(65) Prior Publication Data
US 2009/0182209 A1 Jul. 16, 2009

Related U.S. Application Data (60) Provisional application No. 60/729,339, filed on Oct. 21, 2005, provisional application No. 60/751,009, filed on Dec. 16, 2005.

(51) Int. Cl.
*A61B 5/00* (2006.01)
*A61B 5/1455* (2006.01)

(52) U.S. Cl.
CPC .................................. *A61B 5/14553* (2013.01)
USPC .......................................... 600/323; 600/479

(58) Field of Classification Search
USPC .................................................. 600/323, 479
See application file for complete search history.

(56) References Cited

U.S. PATENT DOCUMENTS

| 4,321,930 | A | * | 3/1982 | Jobsis et al. | 600/344 |
| 4,510,938 | A | * | 4/1985 | Jobsis et al. | 600/344 |
| 5,217,013 | A | * | 6/1993 | Lewis et al. | 600/342 |
| 5,482,034 | A | | 1/1996 | Lewis et al. | |
| 5,584,296 | A | | 12/1996 | Cui et al. | |
| 6,456,862 | B2 | | 9/2002 | Benni | |
| 7,047,055 | B2 | | 5/2006 | Boas et al. | |
| 7,072,701 | B2 | | 7/2006 | Chen et al. | |
| 7,865,223 | B1 | * | 1/2011 | Bernreuter | 600/323 |
| 2002/0016536 | A1 | * | 2/2002 | Benni | 600/323 |
| 2005/0030761 | A1 | * | 2/2005 | Burgess | 362/555 |

FOREIGN PATENT DOCUMENTS

DE 3235998 3/1984

* cited by examiner

*Primary Examiner* — Max Hindenburg
*Assistant Examiner* — Renee Danega
(74) *Attorney, Agent, or Firm* — O'Shea Getz P.C.

(57) ABSTRACT

A near infrared spectrophotometric (NIRS) sensor assembly for non-invasive monitoring of blood oxygenation levels in a subject's body is provided that includes a pad, at least one light source, a near light detector, a far light detector, and a cover. The light source is operative to emit near infrared light signals of a plurality of different wavelengths. The near light detector is separated from the light source by a first distance that is great enough to position the first light detector outside of an optical shunt field extending out from the light source. The far light detector is substantially linearly aligned with the near light detector and light source, and is separated from the near light detector by a second distance, wherein the second distance is greater than the first distance.

5 Claims, 4 Drawing Sheets

METHOD AND APPARATUS FOR SPECTROPHOTOMETRIC BASED OXIMETRY

This invention was made with Government support under Contract No. 2R44NS45488-01 awarded by the Department of Health & Human Services. The Government has certain rights in the invention.

Applicant hereby claims priority benefits of PCT Patent Application no. PCT/US06/41268 filed Oct. 18, 2006 which claims priority to U.S. Provisional Patent Application No. 60/729,339 filed Oct. 21, 2005 and U.S. Provisional Patent Application No. 60/751,009 filed Dec. 16, 2005, the disclosures of which are herein incorporated by reference.

BACKGROUND OF THE INVENTION

1. Technical Field

This invention relates to methods and apparatus for non-invasively determining biological tissue oxygenation utilizing near-infrared spectroscopy (NIRS) techniques in general, and to sensors for use with such techniques in particular.

2. Background Information

Near-infrared spectroscopy is an optical spectrophotometric method that can be used to continuously monitor tissue oxygenation. The NIRS method is based on the principle that light in the near-infrared range (700 nm to 1,000 nm) can pass easily through skin, bone and other tissues where it encounters hemoglobin located mainly within micro-circulation passages; e.g., capillaries, arterioles, and venuoles. Hemoglobin exposed to light in the near-infrared range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored. The ability to continually monitor cerebral oxygenation levels, for example, is particularly valuable for those patients subject to a condition in which oxygenation levels in the brain may be compromised, leading to brain damage or death.

NIRS type sensors typically include at least one light source and one or more light detectors for detecting reflected or transmitted light. The light signal is created and sensed in cooperation with a NIRS system that includes a processor and an algorithm for processing signals and the data contained therein. U.S. Pat. No. 7,047,054, which is commonly assigned with the present application to CAS Medical Systems, Inc. of Branford, Conn., discloses an example of such a sensor. Light sources such as light emitting diodes (LEDs) or laser diodes that produce light emissions in the wavelength range of 700-1000 nm are typically used. A photodiode or other light detector is used to detect light reflected from or passed through the tissue being examined. The NIRS System cooperates with the light source(s) and the light detectors to create, detect and analyze the signals in terms of their intensity and wave properties. U.S. Pat. No. 6,456,862, and U.S. Pat. No. 7,072,701, both of which are commonly assigned to CAS Medical Systems, Inc., of Branford, Conn., disclose a methodology for analyzing such signals. U.S. Pat. Nos. 6,456,862, 7,047,054, and 7,072,701 are hereby incorporated by reference in their entirety.

The light emanating from the light source may be described as traveling along a "mean optical path" through the tissue under examination. The "mean optical path" represents an idealized path traveled by a predominant number of photons emanating from the light source and sensed by the detector, recognizing however that not all photons emanating from the light source will travel the mean optical path. The length of the mean optical path and the depth from the surface reached by the path are a function of the separation distance between the light source and the light detector and the geometry of the path. Several sources of research in NIRS technology provide that the mean optical path follows a "banana-shaped" path.

Meaningful cerebral oxygenation information is collected from light interrogating brain tissue (e.g., passing through, reflecting from, absorbed by, etc.). To non-invasively access the brain tissue, however, the light signal must pass through extracerebral tissue (e.g., scalp, skull, etc.) before and after interrogating the brain tissue. A light signal traveling within any biological medium (e.g., tissue, fluid, etc.) will attenuate, and the amount of attenuation is a function of the medium. In the case of a mean optical path that non-invasively accesses brain tissue, the attenuation attributable to the extracerebral tissue does not yield useful information with respect to the cerebral oxygenation. Consequently, it is desirable to account for the signal attenuation attributable to extracerebral tissue, so that the attenuation attributable to the brain tissue can be distinguished and analyzed.

It is known to use a NIRS sensor, having a pair of light detectors specifically spaced apart from a light source as a means to account for extracerebral tissue; i.e., a first separation distance between the light source and a "near" light detector, and a second separation distance between the light source and a "far" light detector. U.S. Pat. No. 5,482,034, for example, discloses a method for spectrophotometric cerebral oximetry that purports to collect optical response data that represents purely intrinsic brain tissue; i.e., without the effects that result from the interrogating light spectra passing through the structure and substances disposed outwardly of the brain.

According to the '034 patent, light of selected wavelengths is introduced into the subject at a "source" location, and is sensed at first and second light detection locations that are spaced from one another and spaced from the source location by unequal, but preferably comparable and not greatly disproportionate, first and second distances, thereby defining unequal first and second mean optical paths extending between the source and the first and second light detector locations. The mean optical path extending between the source and the near light-detector location is selected so that the internal region encompassed by that mean optical path includes not only the full thickness of the overlying tissue, etc. disposed between the outer surface and the interior region to be examined, but also at least a small portion of the physiological substance disposed within the internal region. The signals sensed at the near detector and at the far detector are then processed to obtain optical response data which particularly characterizes only the tissue of the internal region disposed between the two mean optical paths.

A disadvantage of a method such as that disclosed in the '034 patent is that the two mean optical path lengths of comparable and not greatly disproportionate length limit the amount of tissue interrogation, and therefore the available information.

The '034 patent also identifies and distinguishes the subject matter claimed therein from U.S. Pat. No. 5,217,013, which was issued earlier and assigned to the same assignee as the '034 patent: Somanetics Corporation, of Troy, Mich. According to the '034 patent, the '013 patent discloses a sensor arrangement wherein a near detector is positioned very near a light source, and further discloses an "optimum" light source—near detector separation distance of about eight (8) millimeters, and a light source—far detector separation of about twenty-three (23) millimeters.

The '034 patent "reassesses" and teaches away from the source-receiver positioning disclosed in the '013 patent, however, indicating that the "near" detector should be located at least about twenty to thirty (20-30) millimeters from the source, and the "far" detector should be positioned at least about five to ten (5-10) millimeters distant from the "near" detector; i.e., closer to the "near" detector than to the source. Finally, the '034 patent discloses that locating the "far" detector more than forty (40) millimeters away from the source is not useful as a practical matter, with commercially available and economically feasible components.

The light source—near detector separation distance is not only important relative to the area of interrogation defined by the two optical mean paths, but is also significant relative to signal contamination from the light source itself. An optical shunt field surrounding a light source provides a light path through tissue (usually laterally through the skin surface) without absorption by chromophores such as hemoglobin in blood. The intensity of shunted light within the optical shunt field decreases with increasing distance from the light source. The optical shunt field extends out a distance from the light source, which distance is defined as the point at or beyond which the contamination from the optically shunted light is no longer of significance. If a light detector is placed within the optical shunt field surrounding the light source, the light detected from the shunt field will contain little or no spectrophotometric information of value from biological tissue, and can lead to erroneous calculation of biological tissue oxygenation.

What is needed, therefore, is an improved sensor and method for non-invasively determining the level of oxygen saturation within biological tissue, which sensor is configured to permit interrogation of, and the capture of signal from, a substantial amount of tissue, while at the same time accounting for attenuation attributable to extracerebral tissue, and also a sensor that limits or eliminates undesirable optical shunt effects surrounding the sensor's light source.

DISCLOSURE OF THE INVENTION

According to an aspect of the present invention, a NIRS sensor assembly for non-invasive monitoring of blood oxygenation levels in a subject's body is provided that includes a pad, at least one light source, a near light detector, a far light detector, a component tray, and a cover. The light source is operative to emit near infrared light signals of a plurality of different wavelengths. The near light detector is separated from the light source by a first distance that is great enough to position the first light detector outside of an optical shunt field extending out from the light source. The far light detector is substantially linearly aligned with the near light detector and light source, and is separated from the near light detector by a second distance, wherein the second distance is greater than the first distance. In a preferred embodiment, the light source and detectors are locationally maintained by the component tray.

According to another aspect of the present invention, a method for non-invasively monitoring blood oxygenation levels in a subject's body tissue is provided that includes the steps of: a) providing at least one light source operative to emit near infrared light signals of a plurality of different wavelengths; b) providing a first light detector and a second light detector, both operative to measure light intensity derived from light emitted by the light source and passing through the subject's body tissue; c) positioning the first light detector outside of an optical shunt field extending out from the light source a first distance from the light source; d) positioning the second light detector substantially linearly aligned with the first light detector and the light source, and separated from the first light detector by a second distance, wherein the second distance is greater than the first distance; e) introducing the near infrared light signals into the subject's body tissue; and f) detecting the light resulting from the light introduced into the subject's body tissue, using the first and second light detectors, producing signals representative of such detected light, and processing the signals to obtain data relating to the blood oxygenation level of the subject's body tissue.

An advantage provided by the present method and apparatus is that a desirable amount of subject body tissue can be interrogated relative to that possible with the prior art, while at the same time maintaining an improved signal to noise ratio of the resultant biological parameter of interest; e.g., brain tissue oxygen saturation. The present method and apparatus provides this advantage by positioning the first or "near" light detector outside of an optical shunt field extending out from the light source a first distance from the light source, and positioning the second or "far" light detector substantially linearly aligned with the near light detector and the light source, and separated from the near light detector by a second distance, wherein the second distance is greater than the first distance. The greater second distance increases the amount of "targeted" subject body tissue to be interrogated and improves the noise to signal ratio by increasing the percentage of signal attributable to the targeted tissue. In terms of a cerebral application, the greater second distance increases the amount of brain tissue to be interrogated. The signal to noise ratio is also improved by virtue of the near detector being positioned outside of the optical shunt field extending out from the light source.

According to another aspect of the present invention, the NIRS sensor assembly may include a light source that is rotatably mounted on the component tray.

An advantage of a sensor with a rotatably mounted light source is that it allows the fiber optics to be disposed in a plurality of positions wherein the fiber optics are substantially perpendicular to the direction of the light signal entering the subject. As a result, the sensor assembly is less apt to be accidentally dislodged and the leads can be conveniently moved. At the same time, the light source permits a redirection of a light signal sharper than the minimum bend radius of the fiber optics.

Another advantage of the present invention sensor with a rotatably mounted light source is that a single sensor can be used in applications that historically required left-hand and right-hand sensors. The rotatable connection allows the sensor to be applied, for example, on either the left side or the right side of the subject's forehead without having a lead across the subject's forehead. In fact, in those applications where a pair of sensors is utilized, the leads from both sensors can be rotated toward the top of the subject's head and out of the way of the subject and the attending healthcare worker.

These and other features and advantages of the present invention will become apparent in light of the drawings and detailed description of the present invention provided below.

DETAILED DESCRIPTION OF THE INVENTION

Referring now to the drawings, an embodiment of a NIRS sensor assembly 10 is shown in FIGS. 1-4. The NIRS sensor assembly 10 includes a pad 12, a light source 14, a near light detector 16, a far light detector 18, a component tray 20, and a cover 22. The NIRS sensor assembly 10 is adapted for use with a NIRS system 24 that includes a processor 26 for providing signals to and/or receiving signals from the NIRS sensor assembly 10. For purposes of providing a detailed description of the present NIRS sensor assembly 10, the sensor assembly 10 will be described herein as being used in connection with the NIRS system 24 described in U.S. Pat. No. 6,456,862 and U.S. Pat. No. 7,071,701, which are examples of acceptable NIRS systems. The NIRS sensor assembly 10 is not, however, limited to use with any particular NIRS system.

The pad 12 includes a first aperture 28 for receiving the light source 14, a second aperture 30 for receiving the near light detector 16, and a third aperture 32 for receiving the far light detector 18. In alternative embodiments, the pad 12 could be segmented into two or more independent sections. The pad 12 further includes a subject side 34 and a component side 36. The subject side 34 includes an adhesive surface that may be formed, for example, by the application of an adhesive or a tape to the subject side 34. The pad 12 material is preferably made from a material (e.g., foam) that substantially or completely blocks the transmission of light energy through the pad 12. The pad 12 may be attached on its component side 36 to the cover and/or the component tray 20.

Figure 1:
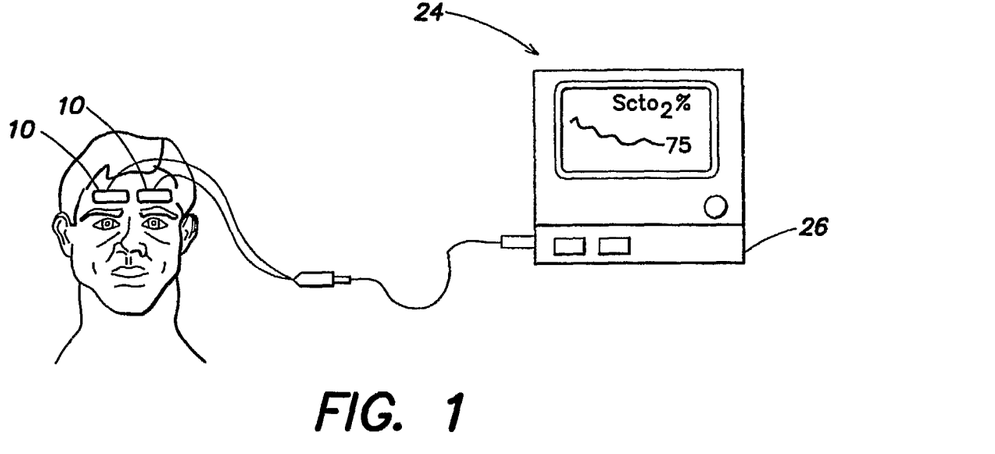
FIG. 1 is a simplified diagrammatic representation of a NIRS sensor placed on a subject's head and coupled to a NIRS system.
Figure 2:
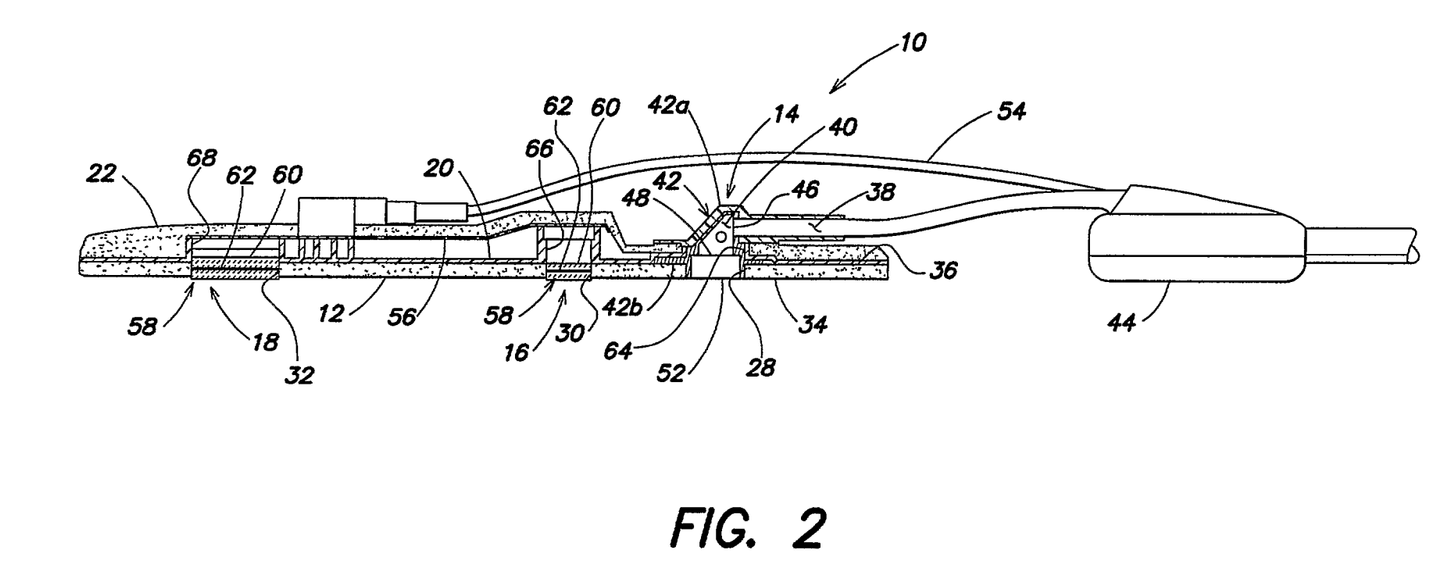
FIG. 2 is a diagrammatic cross-section of a NIRS sensor assembly embodiment.
Figure 3:
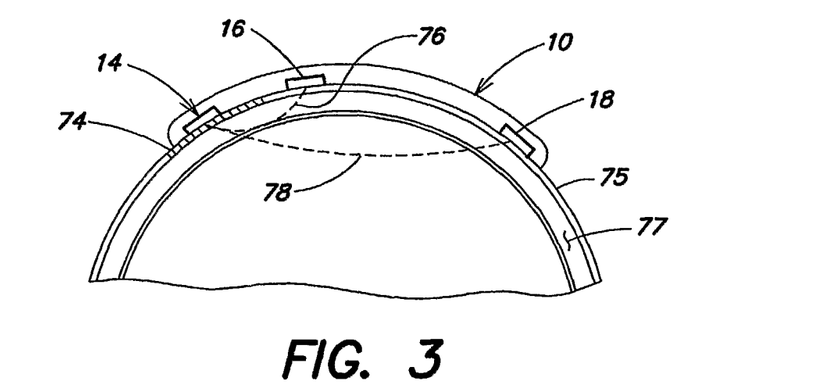
FIG. 3 is a diagrammatic representation of a NIRS sensor placed on a subject's head.
Figure 4:
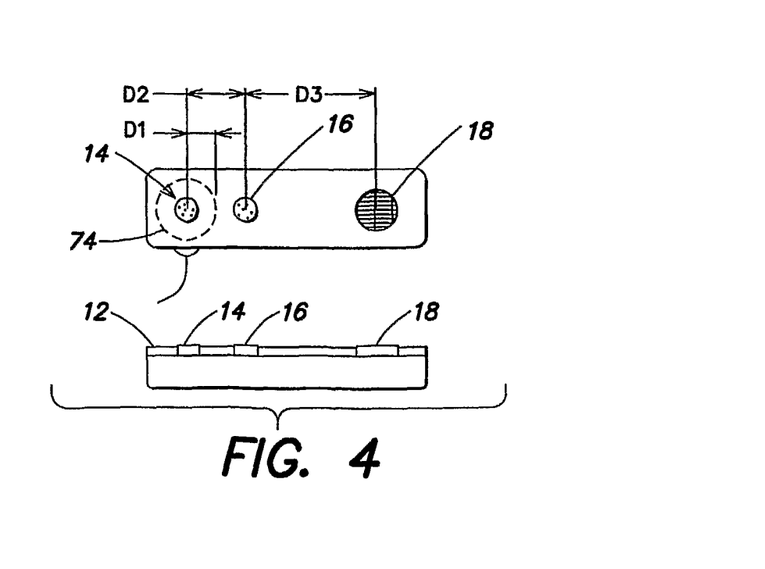
FIG. 4 is a diagrammatic planar view of the subject side of a NIRS sensor, and a side view of the same.
Figure 6:
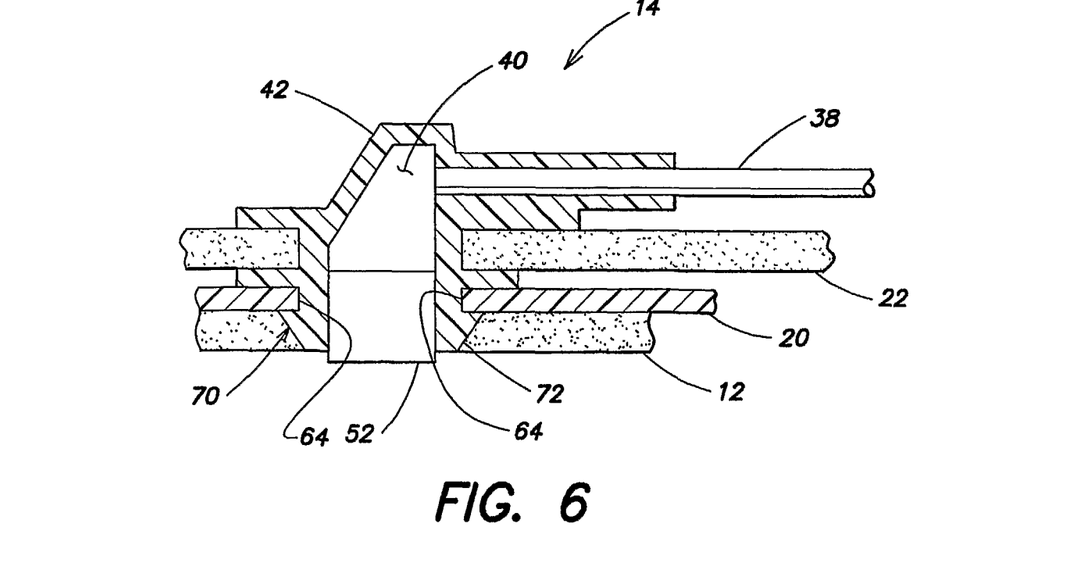
FIG. 6 is a diagrammatic view of a light source within a NIRS sensor assembly.

The light source 14 is selectively operable to guide or emit infrared light. In preferred embodiments, the light source 14 is an assembly that includes a fiber optic light guide 38 (hereinafter referred to as "fiber optics 38"), a light redirecting prism 40, and a housing 42. FIG. 2 shows a housing 42 embodiment having a plurality of elements 42a, 42b. The housing 42 embodiment shown in FIG. 6 (described below) is a one-piece embodiment. The present invention is not limited to either housing embodiment. One end of the fiber optics 38 is optically connected to the light redirecting prism 40. The other end of the fiber optics 38 is disposed within a connector 44 that permits the fiber optics 38 to be optically coupled to fiber optics 38 connected to the NIRS system 24. Acceptable connector 44 embodiments are disclosed below. The prism 40 and a portion of the fiber optics 38 are mounted within the housing 42. The housing 42 helps to protect the optical connection between the fiber optics 38 and the prism 40. The housing 42 also includes features that permit the housing 42, and therefore the light source 14, to be rotatably mounted to the NIRS sensor assembly 10. Additional details regarding the rotatable light source 14 are provided below.

In the above-described preferred embodiments, the light source 14 does not create a light signal itself. Rather, a light signal or signals (collectively referred to hereinafter as a light signal) is introduced into the fiber optics 38 at a position external of the NIRS sensor assembly 10, and is guided into the sensor assembly 10 via the fiber optics 38. The present invention NIRS sensor assembly 10 is not limited to use with any particular method and/or apparatus for introducing a light signal into the fiber optics 38. U.S. Pat. No. 7,047,054, commonly assigned with the present application and incorporated by reference above, discloses an acceptable example of an apparatus for introducing light energy into the fiber optics 38 that includes the use of laser diodes.

A light signal exits the fiber optics 38 and enters the prism 40 through an entrance face 46 and is redirected out of the prism 40 through an exit face 48. The fiber optics 38 can be connected to the entrance face 46 of the prism 40 in a variety of different ways. For example, the fiber optics 38 can be butted against the entrance face 46 of the prism 40 and held in place by a layer of clear epoxy disposed between the prism 40 and the fiber optics 38. In some embodiments, the prism 40 may be disposed within the NIRS sensor assembly 10 so that it is in contact with the subject's skin during use of the NIRS sensor assembly 10. The prism 40 is rigid so that when it is pressed against the subject's skin 50 during the monitoring of blood oxygen, the surface of the skin 50 is flattened, and the distance between the fiber optic output and the skin surface via the prism 40 is constant across the entire illuminated area of the skin 50.

In some embodiments, a light guide 52 having a predetermined thickness is disposed adjacent the exit face 48 of the prism 40, and may be adhered to the exit face 48. A light signal exiting the prism 40 through the exit face 48 will pass through the light guide 52. In these embodiments, the light guide 52 attached to the exit face 48 provides a defined light path geometry between the prism 40 and the subject's skin 50. In some embodiments, the light guide 52 may be disposed within the NIRS sensor assembly 10 so that it is in contact with the subject's skin during use of the NIRS sensor assembly 10. The light guide 52 is rigid so that when it is pressed against the subject's skin 50 (see FIG. 5) during the monitoring of blood oxygen, the surface of the skin 50 is flattened, and the distance between the fiber optic output and the skin surface via the prism 40 is constant across the entire illuminated area of the skin 50.

Figure 5:
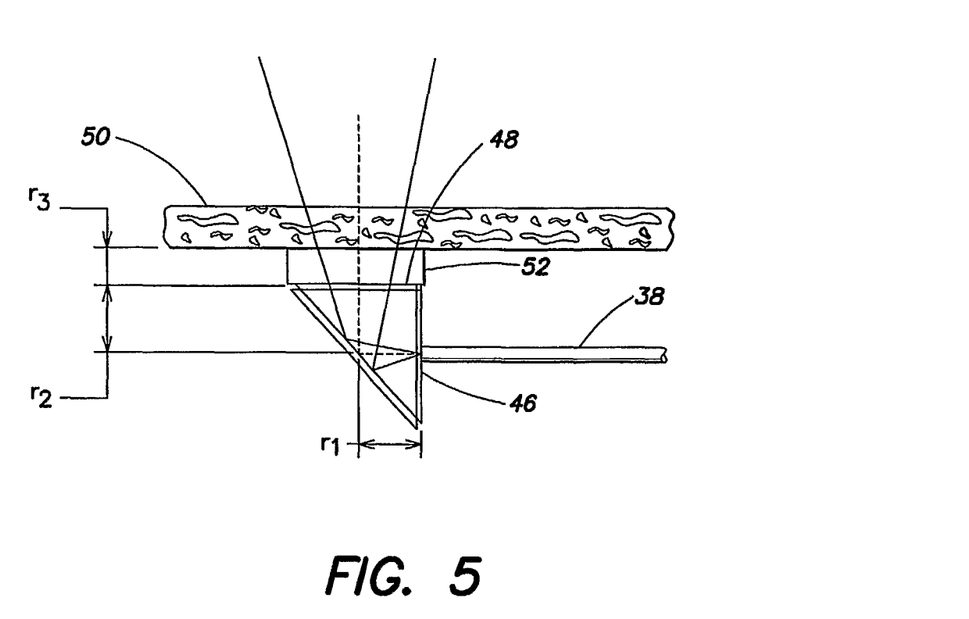
FIG. 5 is a diagrammatic view of light exiting fiber optics and passing through a light prism and light guide.

The arrangements of the light guide 52 and prism 40 shown in FIG. 5 illustrate how the distance "r" between the output of the fiber optics 38 and the surface of the subject's skin 50 can be controlled. As indicated above, it is noted that the planar surface of the light guide 52, when pressed against a subject's skin 50, will flatten the contacted area of the subject's skin 50 so that the distance "r" between the laser coupled fiber optics 38 and the subject's skin 50 is constant for the entire skin area which is illuminated by the light guide 52. The inclusion of the light guide 52 with the prism 40 results in the effective length of "r" since $r = r_1 + r_2 + r_3$. The effective length "r" is significant because the light signal exiting the fiber optics 38 diverges upon exit. The amount the light signal diverges can be controlled by altering the effective length "r". Thus, with the present light guide 52 and prism 40 arrangement, a light signal having a desired light intensity can be accurately and uniformly delivered to the subject's skin. A sensor that has a light source recessed in an open port, in contrast, will likely have some amount of skin bulging into the open port when the port is pressed against the skin. The distance between the skin and the light source will vary across the bulge, thereby increasing the likelihood that the light signal will not be uniformly applied to the skin.

If further attenuation of the laser light field imposed on the subject's skin is desired, then the light guide 52 may include a selective filter. The selective filter may consist of a light-attenuating neutral density filtering element, or a light-diffusive element, such as a milky white semi-transparent plastic material, or both, in combination.

In alternative embodiments, it may be possible to use an LED as a light source rather than a laser diode. Laser diodes and LEDs are fundamentally different, however, from an operational point of view. Consequently, LEDs and laser diodes are not interchangeable and the manner in which an LED could be used as a light source would need to be accounted for prior to an LED being used within the present sensor assembly.

Now referring to FIGS. 1-4, the near light detector 16 and the far light detector 18 each include a light responsive transducer such as a photodiode that is operative to sense light intensity derived from light emitted by the light source 14 after such light passes through the subject's body. The light detectors 16, 18 are electrically connected to a shielded cable 54 that in turn connects the light detectors 16, 18 to the NIRS system 24. In some embodiments, each light detector 16, 18 is attached to a flexible circuit 56, which is in turn connected to the shielded cable 54. The present invention is not, however, limited to the use of a flexible circuit 56.

The NIRS sensor assembly 10 may include an EMI shielding arrangement 58 for each light detector 16, 18. In some embodiments, an EMI shielded and optically transparent pane 60 of predetermined thickness is positioned over the light sensitive surface of each light detector 16, 18. A wire mesh 62 is embedded between two optically transparent members, which together form the pane 60. The mesh 62 will allow at least about 60% optical transmission of the reflected light from the light source 14 after passage through biological tissue to reach the light detector 16, 18. In an alternative EMI shielding embodiment, the wire mesh 62 could be placed directly over the light detector light sensitive surface, and an optically transparent, electrically insulating pane 60 having a predetermined thickness, formed from a material such as glass, could then be placed over the wire mesh 62. The aforesaid shielding arrangements represent examples of acceptable EMI shielding arrangements 58, and the present invention is not limited thereto.

The component tray 20 is a flexible structure that includes a light aperture 64, a near light detector aperture 66, and a far light detector aperture 68. In some embodiments, the apertures 64, 66, 68 all include walls that extend substantially parallel to the axis of the aperture, and therefore have a constant cross-section in an axial direction. The light source 14 and light detectors 16, 18 are locationally maintained relative to the apertures 64, 66, 68. The present invention is not limited to any particular apparatus for locationally maintaining the light source 14 and light detectors 16, 18 relative to the apertures 64, 66, 68. For example, in some embodiments the component tray 20 may include one or more mechanical fasteners, or portions thereof, adjacent an aperture(s) for connecting one or more of the light source 14 and light detectors 16, 18 together with the component tray 20. In another example, one or more of the light source 14 and light detectors 16, 18 may be adhered to the component tray 20.

Figure 7:
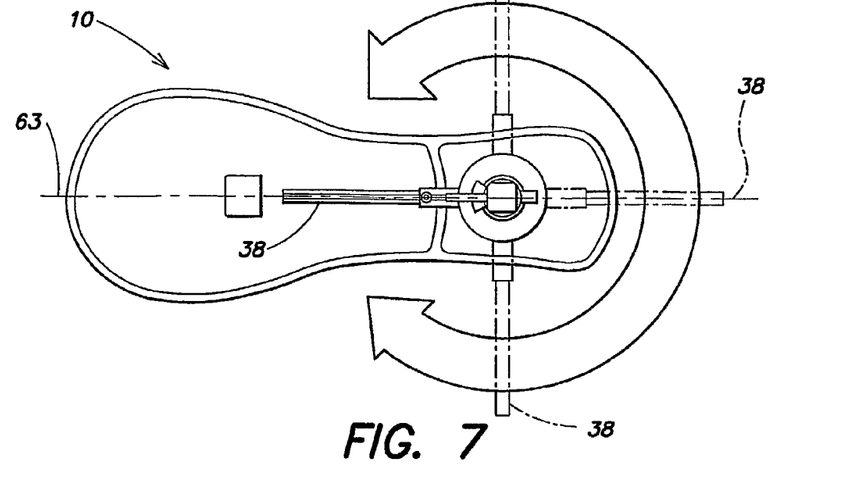
FIG. 7 is a diagrammatic view of a NIRS sensor assembly, illustrating the rotation of the light source.
Figure 8:
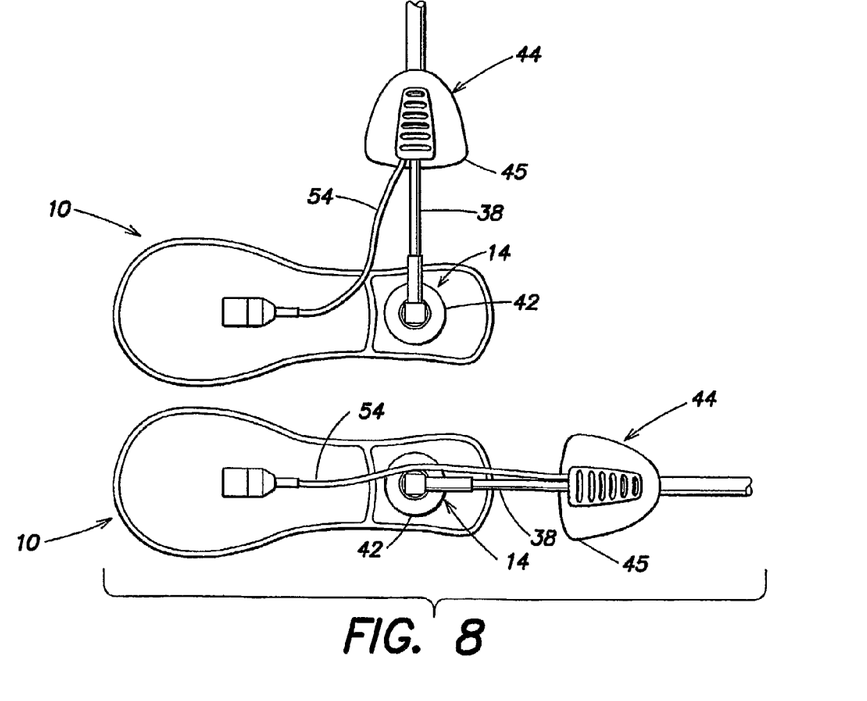
FIG. 8 is a diagrammatic view of a NIRS sensor assembly, illustrating the shielded cable of the detectors and the light source rotated in two different positions.

In some embodiments, the light source 14 is rotatably mounted relative to the other elements of the NIRS sensor assembly 10. The rotatable connection is advantageous because it permits the NIRS sensor assembly 10 to be mounted in a variety of positions on the subject with its leads (e.g., fiber optics 38, shielded cable 54, etc.) positioned in a non-objectionable location. In particular, the rotatable connection allows the fiber optics 38 to be disposed substantially perpendicular to an imaginary line 63 extending through the light source 14, and the detectors 16, 18. As a result, the sensor assembly 10 is less apt to be accidently dislodged and the leads can be conveniently moved. An example of a rotatable connection includes a component tray light aperture 64 and a light source 14 with mating asymmetrical shapes. The light source 14 is placed within the light aperture 64 in an aligned position and subsequently rotated. The asymmetrical shapes of the light source 14 and light aperture 64 permit rotation and at the same time prevent decoupling of the light source 14 and component tray 20 in every circumferential position except for the original alignment position, which position is not typically assumed during normal operating conditions. For example, FIG. 7 diagrammatically shows the light source 14 in the attachment position relative to the rest of the NIRS sensor assembly 10, and shows in phantom the pivotal working range of the light source 14 relative to the NIRS sensor assembly (including the component tray 20). FIG. 8 diagrammatically shows the light source 14 rotated in two different positions and the shielded cable 54 in communication with the detectors.

Alternative rotatable connection configurations include mating pairs 70 (see FIG. 6) where one or both of the mating members include pliable tabs 72 that elastically deflect to permit the coupling, but then return to a position that enables the tabs 72 to keep the light source 14 rotatably mounted within the light aperture 64. The embodiment shown in FIG. 6, for example, has a housing 42 with pliable tabs 72 that mate with the component tray 20. In an alternative embodiment, the component tray 20 may have tabs or other mechanical feature that mate with the housing 42 to permit rotation. The aforesaid embodiments are examples of rotatable connections and the present invention is not limited to these examples.

The relative spacing between the light source 14, near light detector 16 and far light detector 18, and therefore the apertures within the component tray 20, is of considerable importance. As indicated earlier, it is advantageous to improve the signal to noise ratio of the biological parameter of interest, such as brain tissue oxygen saturation, to the extent practically possible. It is our experience that the signal to noise ratio is greatly improved over that associated with prior art NIRS sensors by a spacing that has: 1) a separation distance ("D2") between the light source 14 and the near light detector 16 that is great enough such that the near light detector 16 is positioned outside of any optical shunt field 74 (the shunt field extends a distance "D1" out from the light source 14), and preferably great enough such that the mean optical path extending therebetween extends to the periphery of the extracerebral tissue (e.g., scalp 75, skull 77, etc.); and 2) the separation distance ("D3") between the far light detector 18 and the near light detector 16 is greater than the separation distance between the light source 14 and the near light detector 16 (i.e., D3>D2>D1).

It is also our observation that an optical shunt field 74 will extend outwardly within a subject's skin in a lateral direction from the light source 14 a distance of not more than approximately ten millimeters (10 mm) on average, provided the light source 14 operates within the "Maximum Permissible Exposure" (MPE) values set forth in the American National Standard for the safe use of lasers (ANZ136.1-1993). Other factors such as skin pigmentation may affect the lateral distance of an optical shunt field 74, but as indicated above it is our observation that on average the optical shunt field 74 will extend outwardly within a subject's skin in a lateral direction from the light source 14 a distance of not more than approximately ten millimeters (10 mm).

In view thereof, the spacing between the light source 14 and the near light detector 16 (and therefore the distance between the light source aperture 64 and the near light aperture 66 within the component tray 20) is chosen so that the light source 14 is positioned at least about ten millimeters (10 mm) from the near light detector 16. In a first embodiment of the NIRS sensor assembly 10 intended for use with adults, the light source 14 is positioned approximately fifteen millimeters (15 mm) from the near light detector 16. In a second embodiment of the NIRS sensor assembly 10 intended for use with pediatric subjects and/or small adults, the light source 14 is positioned approximately twelve millimeters (12 mm) from the near light detector 16. In a third embodiment of the NIRS sensor assembly intended for use with neonate subjects, the light source 14 is positioned approximately ten millimeters (10 mm) from the near light detector 16.

The spacing between and the relative positioning of the near light detector 16 and the far light detector 18 within the component tray 20 is chosen so that: 1) the light source 14, near light detector 16 and the far light detector 18 are substantially linearly aligned with one another; and 2) the separation distance ("D3") between the far light detector 18 and the near light detector 16 is greater than the separation distance ("D2") between the light source 14 and the near light detector 16. A greater distance ("D3") between the near light detector 16 and the far light detector 18 (as compared to the separation distance ("D2") between the light source 14 and the near light detector 16) creates a significant difference between the region defined by the mean optical path 76 extending between the light source 14 and near light detector 16, and the region defined by the mean optical path 78 extending between the light source 14 and the far light detector 18. As a result, the information representing the contrast of the two signals is greater than it would be if the two mean optical paths were closer to one another. In terms of the embodiments described above, the position of the far light detector 18 from the light source 14 is as follows: In the first embodiment of the NIRS sensor assembly 10 intended for use with adults, the light source 14 is positioned in the range of approximately forty-seven to fifty millimeters (47 mm to 50 mm) from the far light detector 18. In the second embodiment of the NIRS sensor assembly 10 intended for use with pediatric subjects and/or small adults, the light source 14 is positioned in the range of approximately forty to forty-three millimeters (40 mm to 43 mm) from the far light detector 18. In the third embodiment of the NIRS sensor assembly 10 intended for use with neonate subjects, the light source 14 is positioned in the range of approximately twenty-five to thirty millimeters (25 mm to 30 mm) from the far light detector 18.

The cover 22 is positioned on the NIRS sensor assembly 10 so that the component tray 20, the light source 14, the near light detector 16, and the far light detector 18 are disposed between the cover 22 and the pad 12. The cover 22 preferably consists of a soft pliable material that can be used in a patient environment. Examples of acceptable cover materials include, but are not limited to, vinyl materials, plastic materials and foam materials. The cover 22 may be attached to the NIRS sensor assembly 10 in a variety of different ways. For example, the cover 22 may be adhered to the component tray 20 and/or the pad 12. The cover material preferably blocks light from entering the NIRS sensor assembly 10.

In preferred embodiments, the NIRS sensor assembly 10 includes a connector 44 that allows for attachment and removal of the sensor assembly from the NIRS system. The connector 44 includes a fiber optic coupler and a shielded cable coupler. The fiber optic coupler provides an interface for optically connecting the fiber optics 38 of the NIRS sensor assembly 10 to the NIRS system 24. Similarly, the shielded cable coupler provides an interface for connecting the photodiode output of the NIRS sensor assembly 10 to the NIRS system 24. In some embodiments, the connector 44 is a hybrid connector that incorporates the fiber optic coupler and the shielded cable coupler together into a single unit. In other embodiments, the connector 44 includes a fiber optic coupler and a shielded cable coupler that are independent of one another.

In some embodiments, a photodiode preamplifier 45 is used to amplify the light intensity signals derived from light emitted by the light source 14 that passes through the subject's body, and is sensed by the light detectors 16, 18. The preamplifier may be disposed within the connector 44.

In some embodiments, a multi-fiber optic combiner may be used that allows for multiple laser light sources of different wavelengths to be coupled into a small diameter core fiber optic output leading to the NIRS sensor assembly 10. The present invention sensor assembly 10 does not require the use of a multi-fiber optic coupler, and if one is used the present NIRS sensor assembly 10 is not limited to using any particular multi-fiber optic coupler. U.S. Pat. No. 7,047,054, which was earlier incorporated by reference into the present application, discloses an example of an acceptable multi-fiber optic coupler.

The connector 44 can also include sensor identification encoding means so that the NIRS system 24 can identify the type of NIRS sensor assembly 10 connected; i.e., an adult, pediatric, neonate, & other configured sensor. Once the type of sensor is identified, the NIRS system can then select appropriate information for use with that sensor; e.g., calibration information for a specific sensor configuration. Methods of encoding include but are not limited to: 1) setting different resistor values for each differently configured sensor in which the NIRS system can measure the resistance value though a voltage divider circuit; or 2) incorporating a small memory device, such as a serial PROM, which has sensor identification information stored to be read by the NIRS system 24.

In the operation of the present invention, a NIRS sensor assembly is provided that includes at least one light source, a first light detector and a second light detector. The light source is operative to emit near infrared light signals of a plurality of different wavelengths. The first and second light detectors are both operative to measure light intensity values derived from light emitted by the light source that passes through the subject's body tissue. The first light detector is positioned a distance "D2" from the light source. The first light detector is also positioned outside of an optical shunt field extending out from the light source. The shunt field extends out from the light source a distance "D1". The second light detector is substantially linearly aligned with the first light detector and the light source, and separated from the first light detector by a distance "D3". The distance "D3" is greater than the distance "D2". The NIRS sensor assembly embodiments disclosed above facilitate the relative positioning of the light source 14 and light detectors 16, 18.

Once the NIRS sensor assembly 10 is positioned relative to the subject's skin, near infrared light signals are introduced into the subject's body tissue. The light resulting from the light introduced into the subject's body tissue is subsequently detected using the first and second light detectors 16, 19, producing signals representative of such detected light. The signals are relayed back to the NIRS system 24 via the shielded cable 54, where they are processed to obtain data relating to the blood oxygenation level of the subject's body tissue. As stated above, the present invention NIRS sensor assembly 10 is not limited to use with any particular NIRS system.

Since many changes and variations of the disclosed embodiment of the invention may be made without departing from the inventive concept, it is not intended to limit the invention otherwise than as required by the appended claims. For example, the present invention is disclosed in the context of a cerebral application. The present invention is not limited to cerebral oximetry applications and can be used for non-invasive monitoring of blood oxygenation levels in other body tissues and fluids.

What is claimed is:

1. A near infrared spectrophotometric (NIRS) sensor assembly for non-invasive monitoring of blood oxygenation levels in a subject's body tissue, said assembly comprising:
   a flexible pad;
   at least one light source operative to emit near infrared light signals of a plurality of different wavelengths;
   a first light detector operative to measure light intensity values derived from light emitted by the light source and passing through the subject's body tissue, wherein the first light detector is separated from the light source by a first distance of about 15 mm; and
   a second light detector operative to measure light intensity values derived from light emitted by the light source and passing through the subject's body tissue, wherein the second light detector is substantially linearly aligned with the first light detector and the light source, and is separated from the light source by a distance in the range of about 47-50 mm,
   wherein the first light detector is disposed between the light source and the second light detector.

2. The sensor assembly of claim 1, wherein the light source includes one or more light emitting diodes.

3. The sensor assembly of claim 1, wherein one or both of the first and second light detectors include a photodiode and an optically transparent pane disposed contiguous with the photodiode.

4. The sensor assembly of claim 1, further including a connector operable to connect the sensor assembly to a NIRS system.

5. The sensor assembly of claim 4, wherein the connector includes a sensor identification encoder operable to identify the sensor assembly to the NIRS system.

* * * * *